US012622742B2

(12) United States Patent
    Nagtegaal

(10) Patent No.: US 12,622,742 B2
(45) Date of Patent: May 12, 2026

(54) ELECTROSURGICAL INSTRUMENT

(71) Applicant: Gyrus ACMI, INC, Westborough, MA (US)

(72) Inventor: Marno Nagtegaal, Cardiff (GB)

(73) Assignee: GYRUS ACMI, INC, Westborough, MA (US)

( * ) Notice: Subject to any disclaimer, the term of this patent is extended or adjusted under 35 U.S.C. 154(b) by 869 days.

(21) Appl. No.: 17/684,897

(22) Filed: Mar. 2, 2022

(65) Prior Publication Data

US 2022/0287762 A1 Sep. 15, 2022

(30) Foreign Application Priority Data

Mar. 12, 2021 (GB) ...................................... 2103496

(51) Int. Cl.
    *A61B 18/14* (2006.01)
    *A61B 18/00* (2006.01)
    *A61B 18/12* (2006.01)

(52) U.S. Cl.
    CPC ...... *A61B 18/1445* (2013.01); *A61B 2018/00184* (2013.01); *A61B 2018/00404* (2013.01); *A61B 2018/0063* (2013.01); *A61B 2018/0094* (2013.01); *A61B 2018/126* (2013.01); *A61B 2018/146* (2013.01)

(58) Field of Classification Search
    CPC .......... A61B 18/1445; A61B 2018/146; A61B 2018/00184
    See application file for complete search history.

(56) References Cited

U.S. PATENT DOCUMENTS

| | | | |
|---|---|---|---|
| 3,404,683 A | 10/1968 | Eizenberg | |
| 2011/0196368 A1 | 8/2011 | Moses et al. | |
| 2014/0005696 A1* | 1/2014 | Schulz | A61B 17/083 |
| | | | 606/143 |
| 2015/0164526 A1 | 6/2015 | Bernhardt | |
| 2016/0151110 A1* | 6/2016 | Kerr | A61B 18/1442 |
| | | | 606/45 |
| 2019/0357968 A1* | 11/2019 | Boudreaux | A61B 18/1206 |

(Continued)

OTHER PUBLICATIONS

"Sovay's Medical-Grade Ixef PARA Enables Elasso Surgical Instrument to Pioneer a Cutting-Edge New Instrument for Removal of Adenoids and Tonsils", Sep. 19, 2016, Solvay, https://www.solvay.com/sites/g/files/srpend221/files/tridion/documents/20160918-Elasso-Chooses-Ixef-for-Surgical-Tool-EN.pdf (Year: 2016).*

(Continued)

*Primary Examiner* — Linda C Dvorak
*Assistant Examiner* — Ryan T Clark
(74) *Attorney, Agent, or Firm* — Schwegman Lundberg & Woessner. P.A.

(57) ABSTRACT

An improved electrosurgical instrument, specifically a scissor style vessel sealer, comprising two overmoulded jaws formed from a structural polymer held in place by a pivot pin. The moulded structural polymer replaces many metal components which would otherwise be required for such an assembly. Not only does the use of the moulded structural polymer simplify the assembly of the instrument, it also enables the following additional functionality: moulded pivot holes, flanges providing lateral support, and a flexible lever arm which is designed to provide the force needed to clamp and seal vessels.

13 Claims, 7 Drawing Sheets

(56) References Cited

U.S. PATENT DOCUMENTS

2020/0113621 A1    4/2020   Sims et al.

OTHER PUBLICATIONS

Sep. 9, 2024 Examination Report issued British Patent Application
No. GB2103496.2.
Nov. 21, 2024 Examination Report issued in United Kingdom
Patent Application No. GB2103496.2.
Solvay, "Ixef PARA polyarylamide, Specialty Polymers," https://
www.solvay.com/sites/g/files/srpend221/files/2018-10/Ixef-PARA-
Overview_EN-v2.5_0.pdf, pp. 1-5.
Dec. 2, 2021 Search Report issued in British Patent Application No.
2103496.2.

* cited by examiner

ELECTROSURGICAL INSTRUMENT

TECHNICAL FIELD

Embodiments of the present invention described herein relate to an electrosurgical device, and in particular a scissor action vessel sealer.

BACKGROUND TO THE INVENTION AND PRIOR ART

Electrosurgical instruments provide advantages over traditional surgical instruments in that they can be used for coagulation and tissue sealing purposes. Electrosurgical forceps are used to clamp tissue or vessels before cutting and/or sealing the tissue by delivering a coagulation RF signal to one or more electrodes located at the end of the instrument. Vessel sealers currently on the market have a lot of assembly complexity both in terms of the number of components and the materials used to assemble a pair of jaws. Specifically, scissor style vessel sealers on the market use a combination of materials and components to form the jaw and lever arm assemblies. These assemblies involve a lot of metal components which are expensive, require various manufacturing and bonding techniques, as well as insulation from the electrodes. These assembly costs are typically very high due to the many components used.

SUMMARY OF THE INVENTION

Embodiments of the present invention provide an electrosurgical instrument, specifically a scissor style vessel sealer, comprising two overmoulded jaws formed from a structural polymer held in place by a pivot pin. The moulded structural polymer replaces many metal components which would otherwise be required for such an assembly. Not only does the use of the moulded structural polymer simplify the assembly of the instrument, it also enables the following additional functionality: moulded pivot holes, flanges providing lateral support, and a flexible lever arm which is designed to provide the force needed to clamp and seal vessels. No metal reinforcement components are required within the lever arm.

Accordingly, in a first aspect, an electrosurgical instrument is provided, comprising: a first component comprising a distal first jaw member, a first central section and a proximal first arm, the first component being formed from a first single piece of polymer material; a second component comprising a distal second jaw member and a second central section, the second component being formed from a second single piece of polymer material, wherein the central section is connected to a proximal second arm. The first and second components are pivotably connected such that at least one of the first and second arms is movable with respect to the other arm between an open position in which the arms are spaced one from another and a closed position in which the arms are brought closer together, and the first and second jaw members being moveable between first and second conditions in response to the relative movement of the at least one arm. At least the first arm is arranged in use to provide a clamping force to clamp a vessel held between the first and second jaw members, the first arm being flexible past a certain application force.

The above aspect is advantageous as using the polymer overmould replaces many metal components which would otherwise be necessary for such an assembly. Metal components are expensive, require various manufacturing and bonding techniques, and require insulation from electrodes. Using metal components results in high assembly costs due to many components being used. There is no exposed metal within this instrument, apart from the pivot pin and electrodes. The use of the polymer material greatly reduces the complexity of the instrument, reduces the part count and hugely simplifies the assembly.

Using polymer material has further advantages of providing the additional functionality of moulded pivot holes and a flexible lever arm with an integral finger loop. The flexibility of the lever arm can be specially tuned to provide the correct clamping force for clamping and sealing vessels. The correct clamping force is achieved by the lever arm being flexible past a certain application force. As such, if a user applies a great application force which would ordinarily be above the predetermined acceptable range for clamping and/or sealing vessels, the lever arm flexes. This flexing of the lever arm results in the excess force being dissipated, the remaining force is transferred to the jaws such that the correct clamping/sealing force is applied to the vessels/tissue. There are no metal reinforcement components required for the lever arm. The tuning of the flexibility of the lever arm is achieved by designing the thickness of the material that forms the arm to give the desired flexibility, in that the thicker the material the less flexible it will be and the greater force will be transferred to the jaw members before the arm flexes. Both the width and height thickness dimensions may be modulated to give a desired flexibility response.

In some embodiments, a flexibility of the first arm is selected such that the clamping force is within a predetermined range.

In some embodiments, at least one of the first and second jaw members comprises an electrically conductive sealing surface for communicating RF energy through tissue held therebetween, wherein at least one of the first and second arms comprises radio RF electrical connections capable of connecting the electrically conductive sealing surface to a source of RF energy.

In some embodiments, at least one of the first arm and the second arm comprises a finger loop.

In some embodiments, the first and second components are slotted together such that the second component slots through an opening in the first central section of the first component. This is advantageous as it allows the instrument to be assembled quickly and easily, lowering assembly costs.

In some embodiments, the opening is defined by first and second flanges, and the second central section of the second component is held in the opening of the first central section of the first component, the second central section being supported by the first and second flanges. The flanges are an advantageous result of using the polymer material and they provide lateral support and guide the opening and closing of the device.

In some embodiments, the first and second components are pivotably connected using a pivot pin.

In some embodiments, the pivot pin threads through a first pivot hole in the first flange, a second pivot hole in the second central section, and a third pivot hole in the second flange.

In some embodiments, the instrument further comprises an activation button operable to deliver a source of radio frequency (RF) energy to at least one of the first and second jaw members. Having an activation button on the instrument is advantageous the user has direct and easy access to the button, allowing the user to be able to freely activate and deactivate the coagulation function.

In some embodiments, the first and second jaw members comprise a pair of bipolar forceps.

In some embodiments, the first single piece of polymer material and the second single piece of polymer material are formed from a structural polymer overmould having in excess of 50% glass fiber reinforcement, to provide sufficient strength and rigidity, whilst also permitting flexibility for dissipation of excess applied force. In one embodiment a polymer material called PARA IXEF may be used. PARA IXEF is an advantageous choice of structural polymer as it provides a combination of strength and aesthetics. PARA IXEF typically contains around 50-60% glass fiber reinforcement, thus giving strength and rigidity. PARA IXEF has a high resistance to mechanical stresses, high rigidity, and can be used for complex shapes.

A second aspect provides an electrosurgical system, comprising an RF electrosurgical generator, and an electrosurgical instrument as described above.

A third aspect provides a method of assembling an electrosurgical instrument, the method comprising: forming a first component from a first single piece of polymer material, the first component comprising a distal first jaw member, a first central section and a proximal first arm; forming a second component from a second single piece of polymer material, the second component comprising a distal second jaw member and a second central section; connecting the second central section to a proximal second arm;

and pivotally connecting the first and second components together such that at least one of the first and second arms is movable with respect to the other arm between an open position in which the arms are spaced one from another and a closed position in which the arms are brought closer together, the first and second jaw members being moveable between first and second conditions in response to the relative movement of the at least one arm.

This simple assembly method is advantageous as it greatly reduces assembly costs.

In some embodiments, the step of pivotally connecting the first and second components comprises: slotting the second component through an opening in the first central section of the first component; closing the first and second jaw members such that a first pivot hole in the first flange, a second pivot hole in the second central section, and a third pivot hole in the second flange align; and threading a pivot pin through the first, second and third pivot holes such that the first and second components are pivotally connected.

BRIEF DESCRIPTION OF THE DRAWINGS

Embodiments of the invention will now be further described by way of example only and with reference to the accompanying drawings, wherein like reference numerals refer to like parts, and wherein.

DESCRIPTION OF THE EMBODIMENTS

Figure 1:
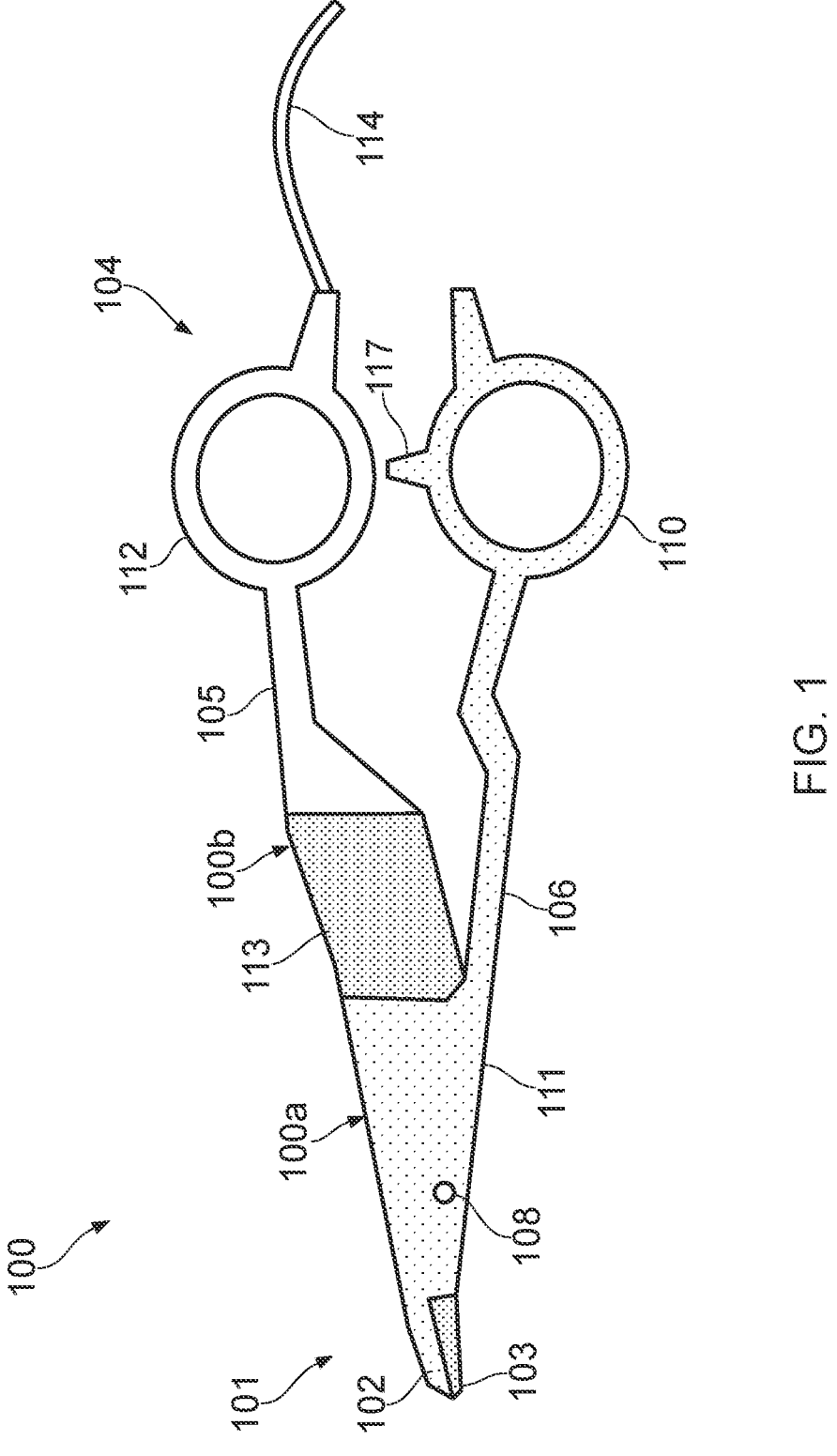
FIG. 1 is a side view of an electrosurgical instrument according to embodiments of the present invention.

Referring to the drawings, FIG. 1 shows an electrosurgical instrument 100 according to a first example of the present invention. The instrument 100 comprises a first component 100a and a second component 100b. The first component 100a is formed of a single piece of polymer material. Likewise, the second component 100b is also formed of a single piece of polymer material. The first component 100a comprises a first jaw member 102, a first central section 111 and a first arm 106. The second component 100b comprises a second jaw member 103 and a second central section 113. The second component 100b may be connected to a second arm 105.

The instrument 100 includes a distal end effector 101 comprising the first jaw member 102 and the second jaw member 103, thereby defining a pair of opposing jaws. At least one of the jaw members 102, 103 is moveable relative to the other between a first open position in which the jaw members 102, 103 are disposed in a spaced relation relative to one another, and a second closed position in which the jaw members 102, 103 cooperate to grasp tissue therebetween. The jaw members 102, 103 are capable of being connected to a source of electrical energy such that the jaws 102, 103 are capable of conducting energy through tissue held therebetween to effect a tissue seal or coagulate. To effect this, the jaw members 102, 103 may comprise one or more electrodes (not shown in FIG. 1) arranged on or as the inner opposed surfaces of the jaw members 102, 103 and which in use have connections to receive an electrosurgical radiofrequency (RF) signal for the sealing or coagulation of tissue.

Figure 4:
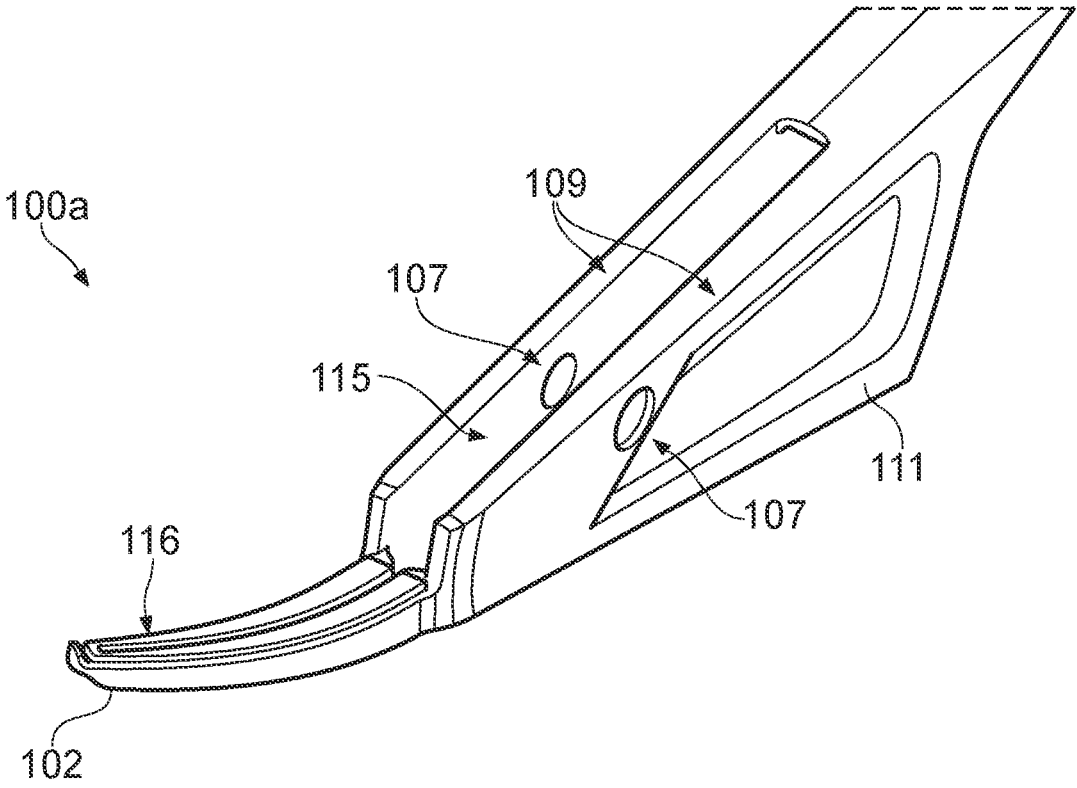
FIG. 4 shows the distal end of the first component in more detail.

The jaw members 102, 103 may also be further provided with a slot or other opening within the inner opposed surfaces through which a mechanical cutting blade (not shown) or the like may protrude, when activated by the user. The jaw members 102, 103 may be curved (as shown best in FIG. 4) so that the active elements of the instrument 100 are always in view. This is important in vessel sealing devices that are used to operate on regions of the body that obscure the user's vision of the device during use.

In this present example, the end effector 101 is actuated using a handle shown generally at 104, wherein the handle comprises the second arm 105 extending from the proximal end of the second jaw member 103, and the first arm 106 extending from the proximal end of the first jaw member 102, the two arms 105, 106 being movable relative to each other. The proximal end of the handle 104 may include a mechanism for actuating each arm 105, 106, for example, a finger loop 110, 112 or the like. The distal end of the two arms 105, 106 are pivotally coupled together through a central or main pivot 108. As such, when the arms 105, 106 are moved relative to each other between a first open position, in which the arms 105, 106 are disposed in a spaced relation relative to one another, and a second closed position, this movement causes a corresponding opening and closing of the jaw members 102, 103.

The electrosurgical instrument 100 may include a powerline 114 to supply RF energy to the end effector 101. The powerline 114 may be connected to either of the first or second arms 105, 106. The electrosurgical instrument 100 may also include a mechanical cutting blade (not shown) coupled to a blade actuator, such as a blade trigger (not shown). The cutting blade may be disposed within one of the arms 105, 106 such that actuation of the blade trigger translates the cutting blade along the respective arm 105, 106 and between the two jaw members 102, 103 to thereby cut any tissue grasped therebetween.

The electrosurgical instrument 100 may also be provided with a switch mechanism. The switch mechanism may comprise an activation button 117 located on the handle 104 for activating the RF signal for coagulating tissue. Additionally or alternatively, the switch mechanism may comprise a footswitch (not shown).

In operation, the arms 105, 106 are manipulated by a user to move the jaw members 102, 103, selectively opening and closing the jaw members 102, 103. The jaw members 102, 103 and arms 105, 106 are moveable through multiple positions, preferably at least three. In a first position, the jaw members 102, 103 and the arms 105, 106 are open so that the distal ends of the first and second jaw members 102, 103 are spaced apart and the proximal ends of the first and second arms 106, 105 are spaced apart. In a second position, the jaw members 102, 103 and arms 105, 106 are closed so that the first and second jaw members 102, 103 are proximate one another, and the first and second arms 106, 105 are proximate one another. In a third position, the jaw members 102, 103 remain closed as in the second position, whilst the arms 105, 106 are clamped shut. In the third position, associated circuitry or contacts may be connected to connect appropriate electrodes of the jaws with associated connections of an electrosurgical generator to supply RF energy to fuse tissue grasped between the jaws 102, 103.

Figure 2:
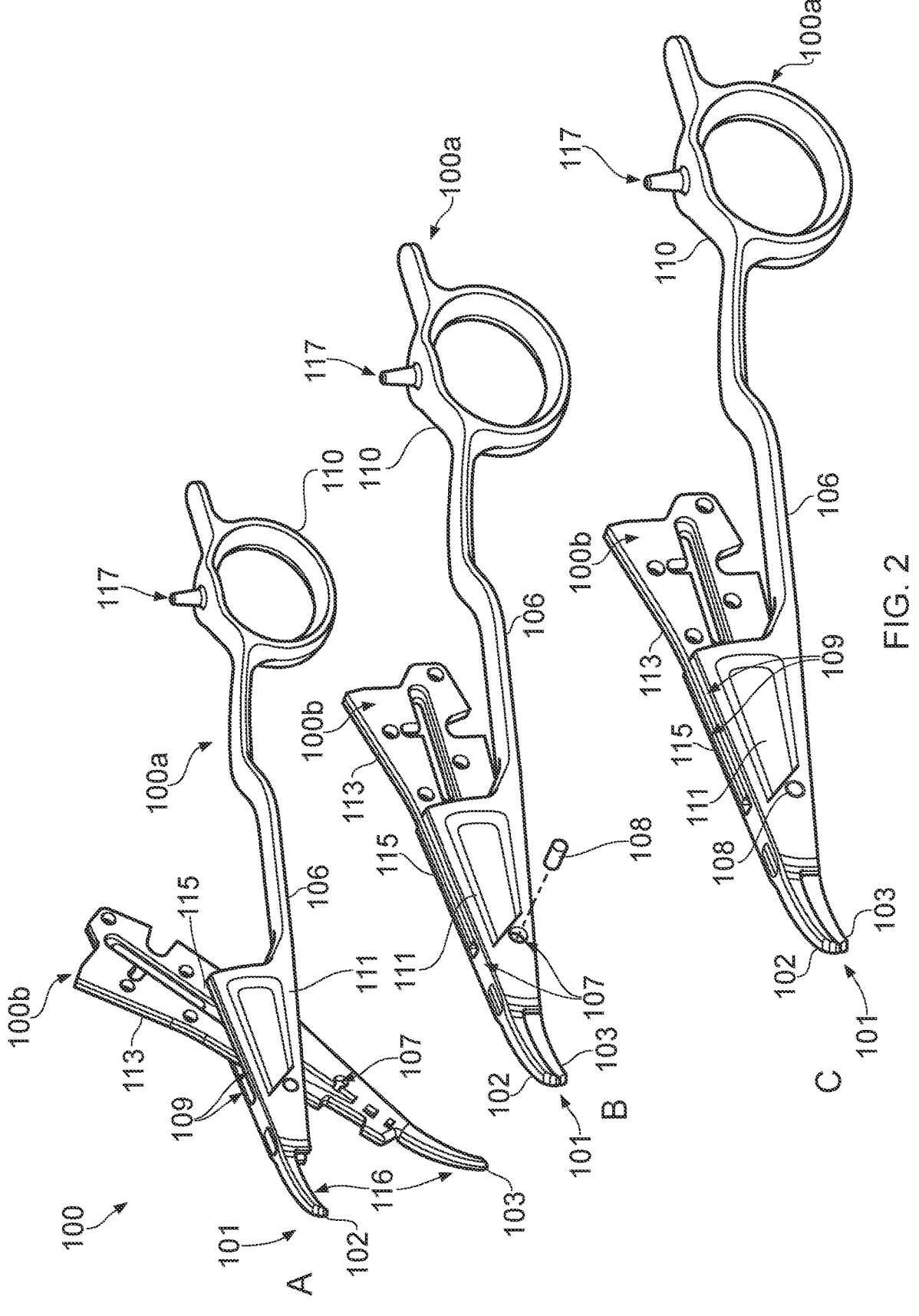
FIG. 2 shows three perspective views of an electrosurgical instrument according to embodiments of the present invention, illustrating how components of the instrument fit together.
Figure 3:
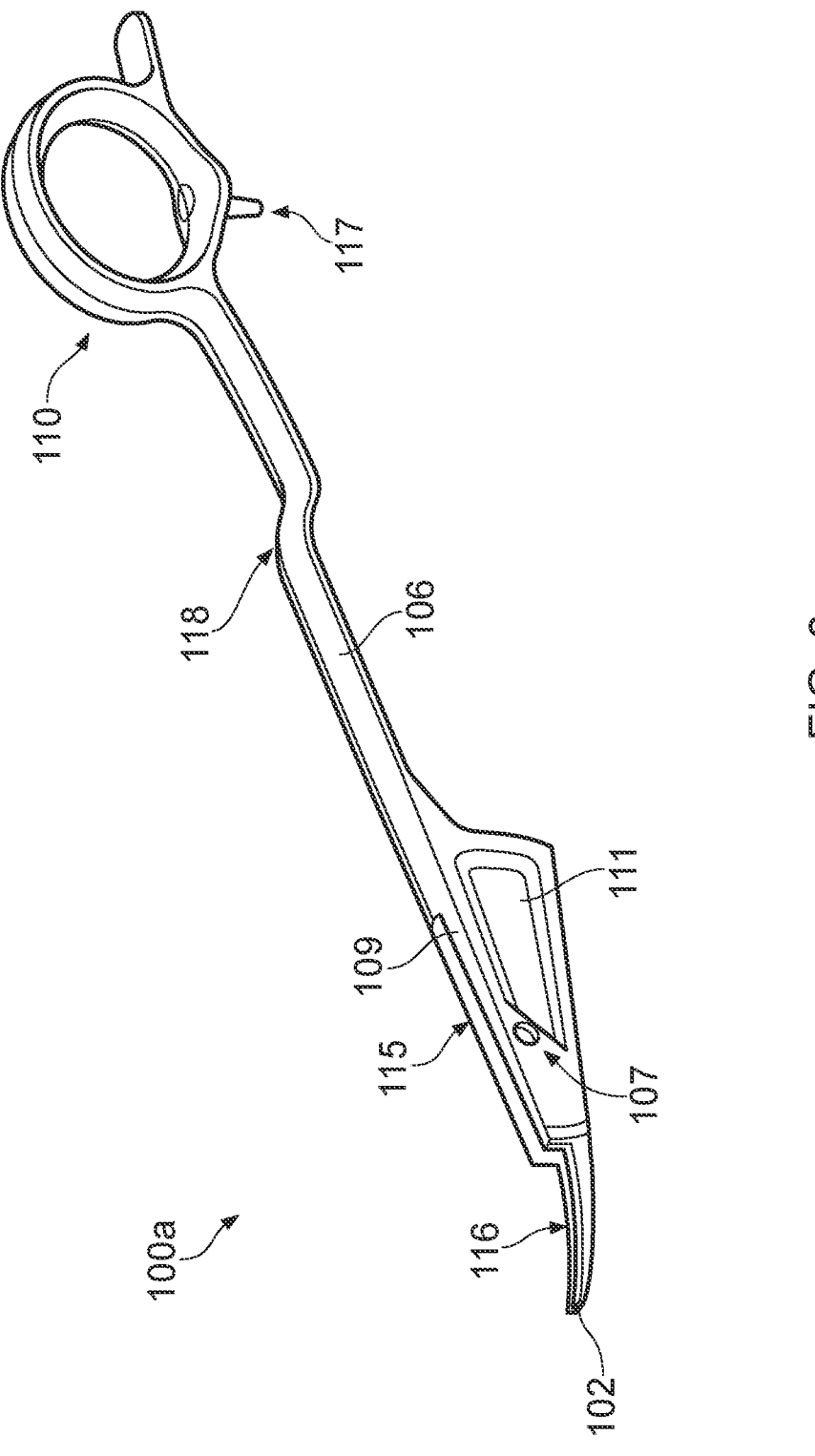
FIG. 3 shows an isolated view of the first component of the electrosurgical instrument.

FIG. 2 shows three perspective views (labelled A, B and C) of an electrosurgical instrument 100 according to embodiments of the present invention, illustrating how the first 100*a* and second 100*b* components fit together. This will be described in more detail below.

The first component 100*a* is shown on its own in FIGS. 3 to 6. The first jaw 102 has an exposed electrode 116 (best shown in FIG. 4) for directing RF energy to fuse tissue grasped between the jaws 102, 103. The first component 100*a* comprises moulded material proximal the jaw member 102 referred to as the first central section 111. The first central section 111 comprises flanges 109 to provide lateral support and guide the opening and closing of the instrument 100. The first component 100*a* further comprises a flexible lever arm (described above as the "first arm") 106 with a bend 118, a finger loop 110 and an activation button 117. The first component 100*a* is formed from one single piece of polymer, i.e. the first jaw 102, the first central section 111, flanges 109, lever arm 106, finger loop 110 and activation button 117 are all formed from one single piece of polymer.

The second jaw 103 may also have an exposed electrode 116 for directing RF energy to fuse tissue grasped between the jaws 102, 103. The second component 100*b* comprises moulded material proximal the jaw member 103 referred to as the second central section 113. The second component 100*b* is formed from one single piece of polymer, i.e. the second jaw 103 and the second central section 113 are formed from one single piece of polymer. The second central section 113 may then be connected to a second arm 105 as in FIG. 1 and described above.

Embodiments of the present invention allow for a simple assembly method which only requires two overmoulded components (the first 100*a* and second 100*b*) to be held together using a pivot pin 108 to form a pair of functional jaws.

As shown in view A of FIG. 2, the first 100*a* and second 100*b* components slot together such that the second component 100*b* slots through an opening 115 in the first central section 111 of the first component 100*a*. In practice, the second central section 113 of the second component 100*b* would be slotted up through the opening 115 in the first component 100*a*, as the curved jaw 103 would prevent the second component 100*b* being slotted down through the opening 115, jaw end first. The opening 115 is defined by first and second flanges 109. The second central section 113 is held in the opening 115, supported by the flanges 109. As shown in view B of FIG. 2, once fitted the jaws 102, 103 come together, which aligns the three polymer pivot holes 107 (one in each flange 109 of the first component 100*a* and one in the second component 100*b*). The pivot pin 108 threads through three pivot holes 107 to hold the assembly together, as shown in view C of FIG. 2. The pivot pin 108 may be either a press-fit pivot pin 108 or a riveted pivot pin 108.

There is no exposed metal within this assembly, apart from the pivot pin 108 and electrodes 116 on both jaws 102, 103. This is advantageous as exposed metal would need to be insulated from the electrodes 116. The polymer used for the first and second components 100*a*, 100*b* of this assembly is PARA IXEF, which acts as a metal replacement in this instance. The use of the polymer greatly reduces the complexity of the product, reduces the part count and greatly simplifies the assembly.

A method of assembly for the instrument 100 will now be described. The method comprises forming the first component 100*a* from a first single piece of polymer material, and the second component 100*b* from a second single piece of polymer material. The second component 100*b* may be connected to the second arm 105. The first and second components, 100*a*, 100*b*, are then pivotably connected together. The components 100*a*, 100*b* may be pivotably connected by slotting the second component 100*b* through the opening 115 in the first central section 111 of the first component 100*a*, closing the first and second jaw members 102, 103, such that a first pivot hole in the first flange, a second pivot hole in the second central section, and a third pivot hole in the second flange align, and threading a pivot pin through the first, second and third pivot holes such that the first and second components 100*a*, 100*b*, are pivotably connected.

The use of the polymer enables overmoulding of the electrodes 116 to form the jaws 102, 103, and also extends the functions of the moulding to include the following additional functionality:

(i) Moulded pivot holes 107.

(ii) Flanges 109 to provide lateral support and guide the opening and closing of the instrument 100.

(iii) Flexible lever arm 106 with an integral finger loop 110, designed to provide the force needed to clamp and seal vessels.

The flexible integral lever arm 106 is part of the first component 100*a*, and therefore part of the same polymer overmoulding. There are no metal reinforcement components within this lever arm 106. The flexible lever arm is described as being the first arm 106, although in practice it could be the second arm 105, or both.

Figure 5:
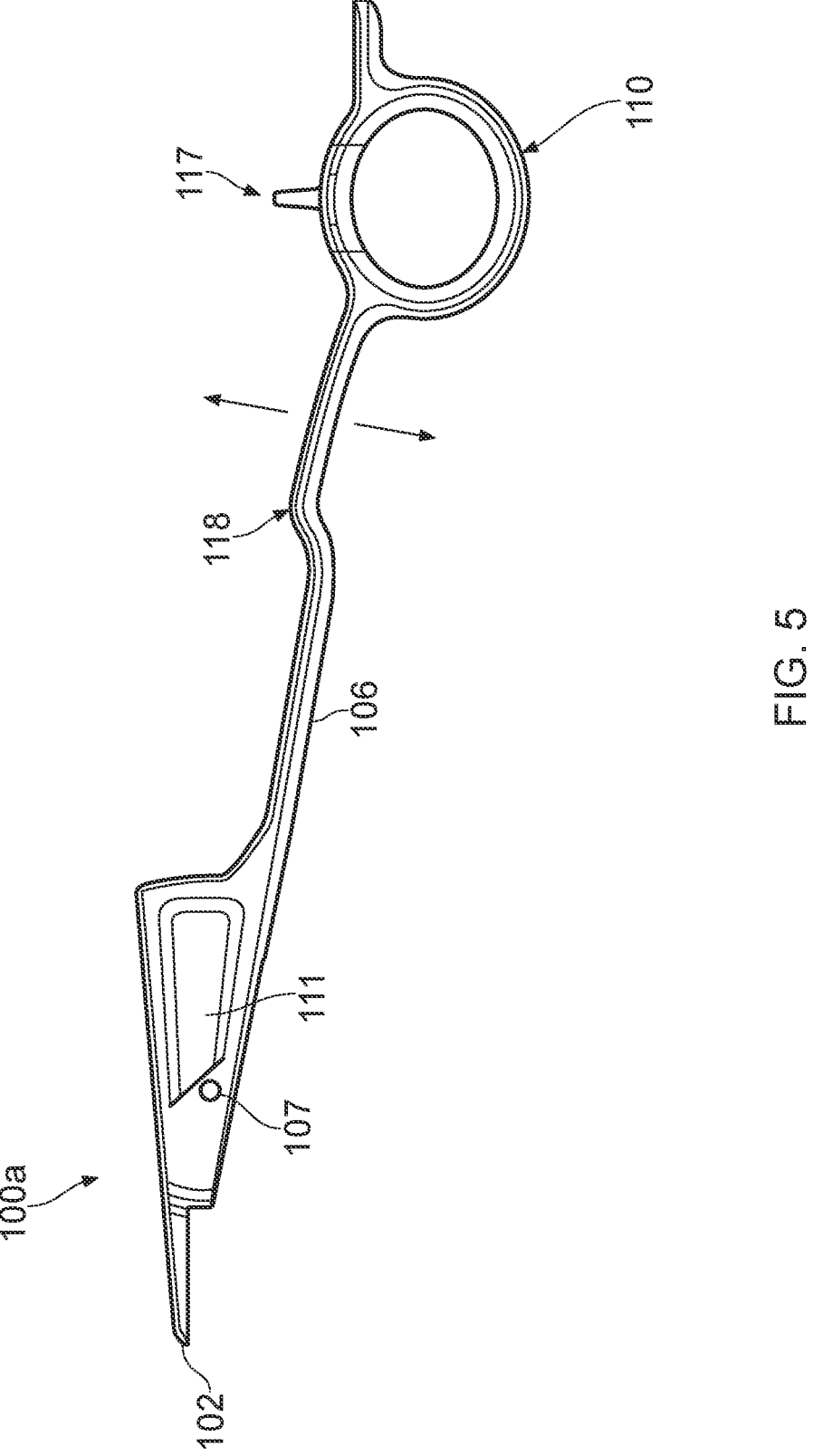
FIG. 5 is a side view of the first component of the electrosurgical instrument.

FIG. 5 shows the first component 100*a* and flexible lever arm 106. The flexibility of the lever arm 106 is specially tuned to provide the correct clamping force for clamping and sealing vessels. The correct clamping force may be considered to comprise a predetermined acceptable range. The correct clamping force is achieved by the lever arm 106 being flexible past a certain application force. As such, if a user applies a great application force which would ordinarily be above the predetermined acceptable range for clamping and/or sealing vessels, the lever arm 106 flexes. This flexing of the lever arm 106 results in the excess force being dissipated, the remaining force is transferred to the jaws 102, 103 such that the correct clamping/sealing force is applied to the vessels/tissue. The more flexible the lever arm 106 is, the less force is transferred to clamp the vessels.

Figure 6:
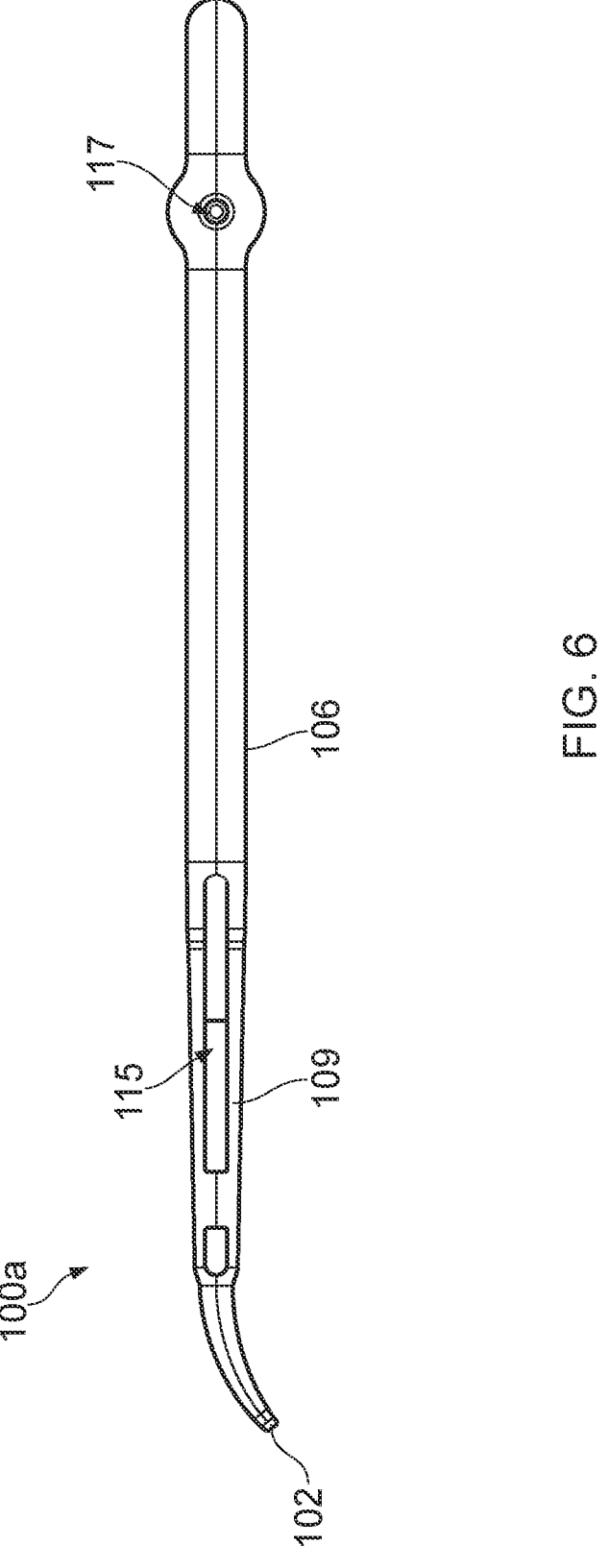
FIG. 6 is a top view of the first component of the electrosurgical instrument.

FIG. 6 is a top view of the first component 100a. The width of the lever arm 106 is specially chosen to provide the correct lateral stiffness for the lever arm. The wider the lever arm 106 is, the stiffer the lever arm 106 is.

As an illustrative worked example, the handles 110, 112 may be approximately three times as far from the pivot 108 as a clamping/sealing location between the jaws 102, 103. This means that the force at the clamping/sealing location would be approximately three times of the applied force at the handles. A correct clamping/sealing pressure may be around 1.5 MPa. For a jaw clamping/sealing area of 2 $cm^2$, the required clamping/sealing force is 300 N. Therefore, the applied force at the handles 110, 112 should be around 100 N.

A typical grip strength of a person may be around 30-40 kg (around 300-400 N). Generally, a surgeon will not use all of their grip strength as an applied force on the handles of the instrument. However, the lever arm 106 is designed to be flexible past a certain application force (e.g. 100 N). As such, if the surgeon applies an application force greater than 100 N, which, were it all to be transferred, would result in a clamping/sealing force greater than 300 N, the lever arm 106 flexes which dissipates the excess force.

The polymer PARA IXEF, which the instrument may be made from, has a flexural strength of around 200 MPa. The flexural strength is equal to the stress in a material just before it breaks in a flexure test. If the desired maximum force is 100 N, then the cross-sectional area of the lever arm 106 must be significantly greater than 0.5 $mm^2$, as at 0.5 $mm^2$, the lever arm 106 would break under 100 N of application force. A suitable cross-sectional area may be 30-50 $mm^2$.

This example makes many simplifying assumptions and is just for illustrative purposes.

Figure 7:
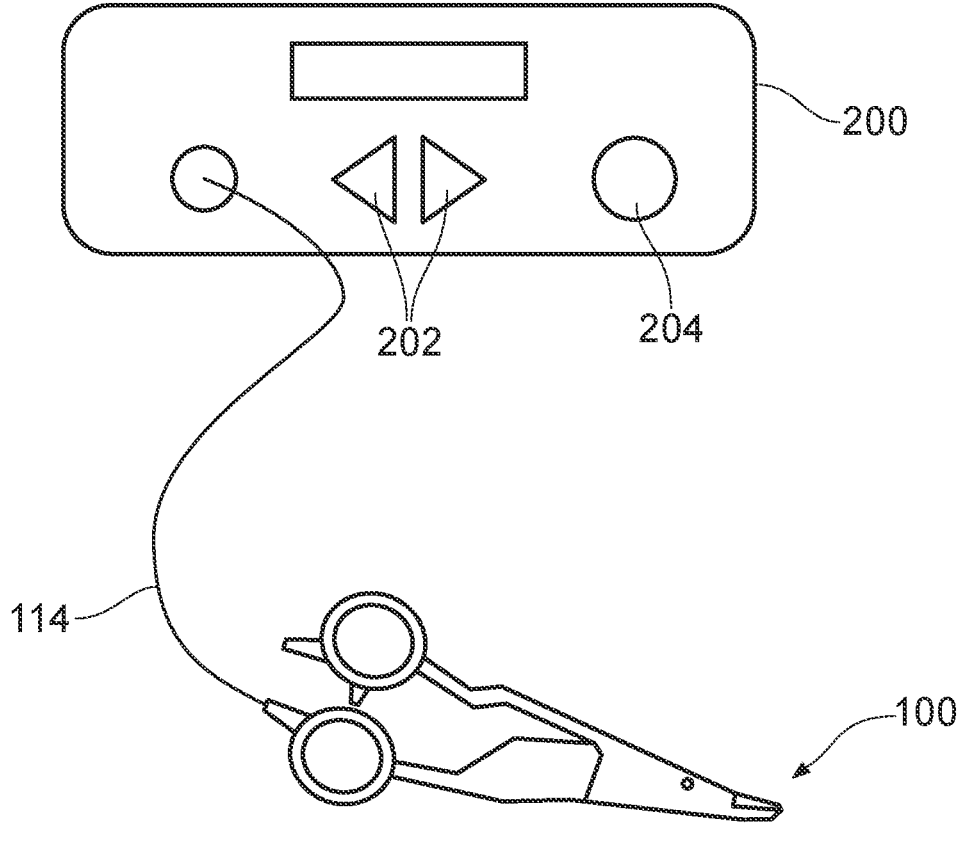
FIG. 7 is a representation of an electrosurgical system including a generator and an instrument in accordance with embodiments of the invention.

Referring now to FIG. 7, the instrument 100 in use is intended for connection to an electrosurgical generator 200 having a controllable RF source therein (not shown) that in use produces an RF coagulation signal that coagulates or seals tissue when applied thereto via the electrodes of the end effector of the instrument 100. Electrosurgical generator 200 includes control input switches 204 and 202, to respectively allow the generator to be turned on and off, and to allow the power of the RF coagulation signal fed to the instrument 100 to be controlled. In these respects, the electrosurgical generator 200 is conventional.

The instrument 100 is connected in use to generator 200 by control and power line 114, which contains separate electrical lines to allow an RF signal to be fed to the end effector of the instrument 100 via internal wiring, and also to allow a control signal to be received to command the electrosurgical generator to output an RF coagulation signal to the instrument 100. This control signal may be initiated by an activation button 117 on the instrument 100, or by a footswitch (not shown). In use the surgeon activates the generator via on-off switch 204, and selects the coagulation or sealing signal strength to be generated by the internal RF source using buttons 202. During a surgical procedure with the instrument when a sealing or coagulation RF signal is required at the end effector, the surgeon controls the generator to produce such a signal by pressing the activation button on the instrument (or by using the footswitch), the generated RF signal then being passed via the electrical lines 114 to the end effector. That is, pressing of the activation button in use causes an RF coagulation or sealing signal to be supplied to the appropriate electrodes contained within the end effector.

The jaw members 102, 103 may each have an electrode 116 or conductive pad. In such cases, the conductive pad of the first jaw member 102 and the conductive pad of the second jaw member 103 are electrically coupled to the electrosurgical generator 200 via wires and connectors to supply RF energy to tissue grasped between the conductive pads. The conductive pads are arranged to have opposing polarity. Wires and associated connections may extend from the activation button 117 through the second arm 105 and/or the first arm 106 to the first and second jaw members 102, 103 and the respective connections to the first and second electrodes. The activation button 117 may complete a circuit when actuated by electrically coupling at least two leads together. As such, an electrical path is then established from an electrosurgical generator 200 to an actuator to supply RF energy to the instrument 100.

Various modifications whether by way of addition, deletion, or substitution of features may be made to above described embodiment to provide further embodiments, any and all of which are intended to be encompassed by the appended claims.

The invention claimed is:

1. An electrosurgical instrument, comprising:
   a first component comprising a distal first jaw member, a first central section and a proximal first arm, the first component being formed from a first single piece of polymer material;
   a second component comprising a distal second jaw member and a second central section, the second component being formed from a second single piece of polymer material, wherein:
   the second central section is connected to a proximal second arm;
   the first and second components are pivotally connected such that at least one of the proximal first and second arms is movable with respect to the other of the proximal first and second arms between an open position in which the proximal first and second arms are spaced one from another and a closed position in which the proximal first and second arms are brought closer together, the distal first and second jaw members being moveable between first and second conditions in response to relative movement of the at least one of the proximal first and second arms; and
   at least the proximal first arm is formed of a shape and thickness of the polymer material such that it flexes past a certain application force, the polymer material having a flexural strength of at least 200 MPa and a cross-sectional area of 30-50 $mm^2$, a cross-section of the first arm being taken perpendicular relative to a length of the first arm, whereby in use the distal first and second jaw members provide a clamping force to clamp a vessel held between the distal first and second jaw members, the flexing of the proximal first arm past the certain application force preventing excess clamping force being applied to the vessel.

2. An electrosurgical instrument according to claim 1, wherein a flexibility of the proximal first arm is selected such that the clamping force is within a predetermined range.

3. An electrosurgical instrument according to claim 1, wherein:

at least one of the distal first and second jaw members comprises an electrically conductive sealing surface for communicating RF energy through tissue held therebetween;

at least one of the proximal first and second arms comprises radio RF electrical connections capable of connecting the electrically conductive sealing surface to a source of RF energy.

4. An electrosurgical instrument according to claim 1, wherein at least one of the proximal first arm and the proximal second arm comprises a finger loop.

5. An electrosurgical instrument according to claim 1, wherein the first and second components are slotted together such that the second component slots through an opening in the first central section of the first component.

6. An electrosurgical instrument according to claim 5, wherein:

an opening of the first central section of the first component is defined by first and second flanges, and the second central section of the second component is held in the opening of the first central section of the first component, the second central section of the second component being supported by the first and second flanges.

7. An electrosurgical instrument according to claim 6, wherein the first and second components are pivotably connected using a pivot pin.

8. An electrosurgical instrument according to claim 7, wherein:

the pivot pin threads through a first pivot hole in the first flange;

a second pivot hole in the second central section of the second component; and a third pivot hole in the second flange.

9. An electrosurgical instrument according to claim 1, wherein the first and second components are pivotably connected using a pivot pin.

10. An electrosurgical instrument according to claim 1, further comprising an activation button operable to deliver a source of radio frequency (RF) energy to at least one of the distal first and second jaw members.

11. An electrosurgical instrument according to claim 1, wherein the distal first and second jaw members comprise a pair of bipolar forceps.

12. An electrosurgical instrument according to claim 1, wherein:

the first single piece of polymer material and the second single piece of polymer material are formed from a structural polymer overmould having at least 50% glass fiber therein.

13. An electrosurgical system, comprising:

an RF electrosurgical generator; and an electrosurgical instrument, comprising:

a first component comprising a distal first jaw member, a first central section and a proximal first arm, the first component being formed from a first single piece of polymer material;

a second component comprising a distal second jaw member and a second central section, the second component being formed from a second single piece of polymer material, wherein:

the second central section is connected to a proximal second arm;

the first and second components are pivotably connected such that at least one of the proximal first and second arms is movable with respect to the other arm between an open position in which the proximal first and second arms are spaced one from another and a closed position in which the proximal first and second arms are brought closer together, the distal first and second jaw members being moveable between first and second conditions in response to relative movement of at least one of the proximal first and second arms; and at least the proximal first arm is formed of a shape and thickness of the polymer material such that it flexes past a certain application force, the polymer material having a flexural strength of at least 200 MPa and a cross-sectional area of 30-50 mm$^2$, a cross-section of the first arm being taken perpendicular relative to a length of the first arm, whereby in use the distal first and second jaw members provide a clamping force to clamp a vessel held between the first and second jaw members, the flexing of an at least first arm past the certain application force preventing excess clamping force being applied to the vessel.

* * * * *